(12) United States Patent
Hemmes et al.

(10) Patent No.: US 6,373,871 B1
(45) Date of Patent: Apr. 16, 2002

(54) ELLIPSOMETER WITH TWO LASERS

(75) Inventors: Klaas Hemmes, Leiden; Karl Richard Koops, Delft, both of (NL)

(73) Assignee: Technische Universiteit Delft, Delft (NL)

(*) Notice: Subject to any disclaimer, the term of this patent is extended or adjusted under 35 U.S.C. 154(b) by 0 days.

(21) Appl. No.: 09/423,448

(22) PCT Filed: May 8, 1998

(86) PCT No.: PCT/NL98/00258

§ 371 Date: Jan. 7, 2000

§ 102(e) Date: Jan. 7, 2000

(87) PCT Pub. No.: WO98/52019

PCT Pub. Date: Nov. 19, 1998

(30) Foreign Application Priority Data

May 9, 1997 (NL) .............................................. 1006016

(51) Int. Cl.$^7$ .............................. H01S 3/10; H01S 3/13
(52) U.S. Cl. ........................ 372/28; 372/9; 372/29.01; 356/484
(58) Field of Search .............................. 372/28, 9, 27; 359/189; 356/484

(56) References Cited

U.S. PATENT DOCUMENTS

| | | | | |
|---|---|---|---|---|
| 5,293,213 A | * | 3/1994 | Klein et al. | 356/349 |
| 5,396,361 A | * | 3/1995 | Sasaki et al. | 359/189 |
| 6,052,186 A | * | 4/2000 | Tsai | 356/349 |

FOREIGN PATENT DOCUMENTS

| | | | |
|---|---|---|---|
| EP | 0 352 747 | | 1/1990 |
| NL | 9202303 | | 7/1994 |
| NL | WO-9416310 | * | 7/1994 |

* cited by examiner

Primary Examiner—Frank G. Font
Assistant Examiner—Armando Rodriguez
(74) Attorney, Agent, or Firm—Young & Thompson

(57) ABSTRACT

Ellipsometer having a light source (L1, L2) which during operation provides a first light beam ($g_1$) having a first angular frequency ($\omega_1$) and a second light beam ($g_2$) having a second angular frequency ($\omega_2$), a neutral beam splitter N having a front face for receiving and at least partially transmitting a measurement beam ($g'_{m2}$), which, during operation, is produced by scanning a sample (S; OD1, OD2) with the second light beam ($g_2$), and a rear face for receiving the first light beam ($g_1$). During operation, the measurement beam ($g'_{m2}$) interferes with the first light beam ($g_1$) at the rear face and an interference beam is thus formed. A unit (W1) receives the interference beam, separating the orthogonal components of the interference beam and providing two alternating voltages (V1, V2) corresponding thereto. The light source comprises a first laser source (L1) for only producing the first light beam ($g_1$) and a separate laser source (L2) for only producing the second light beam ($g_2$). The ellipsometer is also provided with a control circuit (C) having at least one input for receiving information with regard to either the first and second angular frequencies ($\omega_2$, $\omega_1$) or the difference between the first an second angular frequencies and at least one output, coupled at least to one of the two laser sources, for controlling the difference between the first and second angular frequencies ($\omega_2$, $\omega_1$).

7 Claims, 3 Drawing Sheets

ELLIPSOMETER WITH TWO LASERS

FIELD OF THE INVENTION

The present invention relates to an ellipsometer at least comprising light source means which during operation provide a first light beam having a first angular frequency and a second light beam having a second angular frequency, a neutral beam splitter having a front face for receiving and at least partially transmitting a measurement beam, which, during operation, is produced by scanning a sample with the second light beam, and a rear face for receiving the first light beam, wherein, during operation, the measurement beam interferes with the first light beam at the rear face and an interference beam is thus formed, a unit for receiving the interference beam, separating the orthogonal components of the interference beam and providing two alternating voltages corresponding thereto.

BACKGROUND OF THE INVENTION

An ellipsometer of this type is disclosed in International Patent Application WO-A 94/16310 (PCT/NL 93/00283), originating from the Applicant. In said known ellipsometer the light source means comprise a single Zeeman laser which during operation generates two beams shifted somewhat in frequency, which beams are both polarised linearly but perpendicular to one another. With the aid of optical elements known per se, said frequency-shifted beams are split into a first light beam having a first angular frequency and a second light beam having a second angular frequency. The second light beam is used to scan a sample, as a result of which a measurement beam is produced which is incident on the front face of the non-polarising beam splitter. The first light beam is incident on the rear face of the non-polarising beam splitter. The measurement beam is at least partially transmitted through the non-polarising beam splitter, such that interference with the first measurement beam occurs at the rear face of the non-polarising beam splitter. The interference beam is fed to suitable means for analysing the interference beam in order thus to provide desired ellipsometric parameters.

The use of Zeeman lasers is relatively expensive. Moreover, the difference between the frequencies of the light beams generated by the Zeeman laser is determined by parameters set at the time of production. The difference between these frequencies can no longer be adjusted during operation. This constitutes a barrier to the use of the known ellipsometer for some applications.

U.S. Pat. No. 5,396,361 describes a method for stabilising the difference between two optical frequencies, which method can be used for optical heterodyne or homodyne communication. Various systems for carrying out said method are also described. The known system in general comprises two laser sources for generating a first and a second laser beam. The first and second light beams are combined and a portion of the combined beam is subjected to optical heterodyne detection with the aid of an optical detector and then converted into an electrical signal. Said electrical signal is fed to a first input of a multiplier. A second input thereof is connected to an oscillator which provides a reference signal. By means of multiplication, a signal is produced which has a difference frequency component which is a measure of the difference between the frequencies of the electrical signal and the reference signal. The output of the multiplier is coupled to a frequency discrimination circuit, which detects a change in the difference frequency. The output of said frequency discrimination circuit is coupled to at least one of the two laser sources in order to make the difference between the optical frequencies of the lasers substantially constant.

The applications described and suggested by said U.S. Pat. No. 5,396,361 are all in the field of optical communication systems. Applications in the field of ellipsometry are neither described nor suggested.

OBJECT OF THE INVENTION

An objective of the present invention is to provide an ellipsometer with which samples can be scanned in a simple and relatively inexpensive manner.

SUMMARY OF THE INVENTION

In order to achieve this objective, the invention provides an ellipsometer as described in the preamble, which ellipsometer is characterised in that the light source means comprise two separate laser sources and in that the ellipsometer is also provided with a control circuit having at least one input for receiving information with regard to either the first and second angular frequencies or the difference between the first and second angular frequencies and at least one output, coupled at least to one of the two laser sources, for controlling the difference between the first and second angular frequencies.

In principle, an inexpensive optical read system can be constructed by using such an ellipsometer instead of a large and expensive Zeeman laser, as in the prior art. "Frequency mixing", which occurred when a Zeeman laser was used, is prevented by the use of two different lasers. Consequently: an ellipsometer having a greater absolute accuracy is obtained.

The two different lasers are preferably frequency-stabilised lasers. The difference frequency is obtained by heterodyne mixing in the optical set-up, which difference frequency can be kept at a substantially constant value with the aid of an electronic control circuit which, for example, is based on the principle of the phase-locked loop (PLL).

Compared with the set-up in which a Zeeman laser is used, the number of components can be reduced. For example, polarising beam splitters are no longer needed. Furthermore, the phase difference between the two electrical signals can be determined inexpensively in any known way. This can be effected, for example, using a bridge circuit in which four diodes are incorporated. A phase detector of this type is relatively inexpensive and not sensitive to the precise frequency of the two electrical signals. It is therefore not necessary to impose stringent requirements on the control circuit, with the result that the price thereof can remain relatively low.

The light sources can be diode lasers, for which the frequency of the transmitted laser beam can be controlled. Diode lasers of this type are now in development. The size of the ellipsometer according to the invention can be limited using diode lasers of this type.

In principle, a set-up can be chosen in which the second light beam first scans the surface of the sample before it is incident on the front face of the neutral beam splitter. In a preferred embodiment, however, the ellipsometer according to the invention is characterised in that the front face of the neutral beam splitter is set up to receive the second light beam, at least partially reflect the second light beam in the direction of the sample to be scanned and then receive and at least partially transmit the measurement beam originating from the sample to be scanned.

In one of the embodiments according to the invention, one of the two alternating voltages is fed to the input of the control circuit. Specifically, both alternating voltage signals have a component having an angular frequency which is equal to the difference between the angular frequencies of the first light beam and the second light beam. The difference between these two angular frequencies is thus fed via an electrical signal to the input of the control circuit.

In an alternative set-up, an electrical signal is not fed to the input of the control circuit but the difference between the frequencies of the first light beam and the second light beam is determined by the control circuit itself in that said control circuit receives at its input a first input signal derived from the first light beam and a second input signal derived from the second light beam. A control circuit of this type can be in the form disclosed in the cited U.S. Pat. No. 5,396,361, the optical signals themselves being fed to the control circuit. In the present invention, portions of the first and second light beams can be deflected with the aid of beam splitting techniques known per se and fed to such a control circuit.

The ellipsometer according to the invention has an interesting application in scanning optical information carriers, such as optical discs. For an application of this type, the ellipsometer according to the invention is characterised in that it is provided with a support for supporting such an optical information carrier.

With the known techniques for reading optical information from an optical disc use is made of amplitude differences in measurement beams originating from the optical disc, which measurement beams are produced by exposing the optical disc to a laser beam. With the ellipsometer according to the invention the optical information from an optical disc can be determined with the aid of phase difference techniques, which can provide more accurate information than can amplitude difference techniques.

The essential difference between the known read techniques and the technique of reading with the aid of an ellipsometer is that in the prior art differences in the polarisation state of reflected or transmitted light as a consequence of written bits of information on the optical disc are converted into amplitude changes in a detected signal, which amplitude differences then have to be measured. In the case of the technique proposed here, the information is present as modulation, specifically as phase difference, on a carrier wave which in fact consists of two carrier waves. In principle, a low-noise system can be made in this way because, just as in a radio system, it is possible selectively to tune to the carrier wave frequency, that is to say the difference frequency between the first and second light beams. The detected alternating voltages can, for example, first be filtered by means of a narrow band bandpass filter which transmits only the difference frequency including a small side band, in which the modulation is contained.

BRIEF DESCRIPTION OF THE DRAWINGS

The invention will be explained in more detail below with reference to a few figures, which are not intended to restrict the scope of the invention but merely to serve as illustration.

DETAILED DESCRIPTION OF THE INVENTION

The set-up according to FIG. 1a will now be discussed briefly. For more detailed considerations, reference is made, for example, to the abovementioned International Patent Application WO-A 94/16310.

Figure 1A:
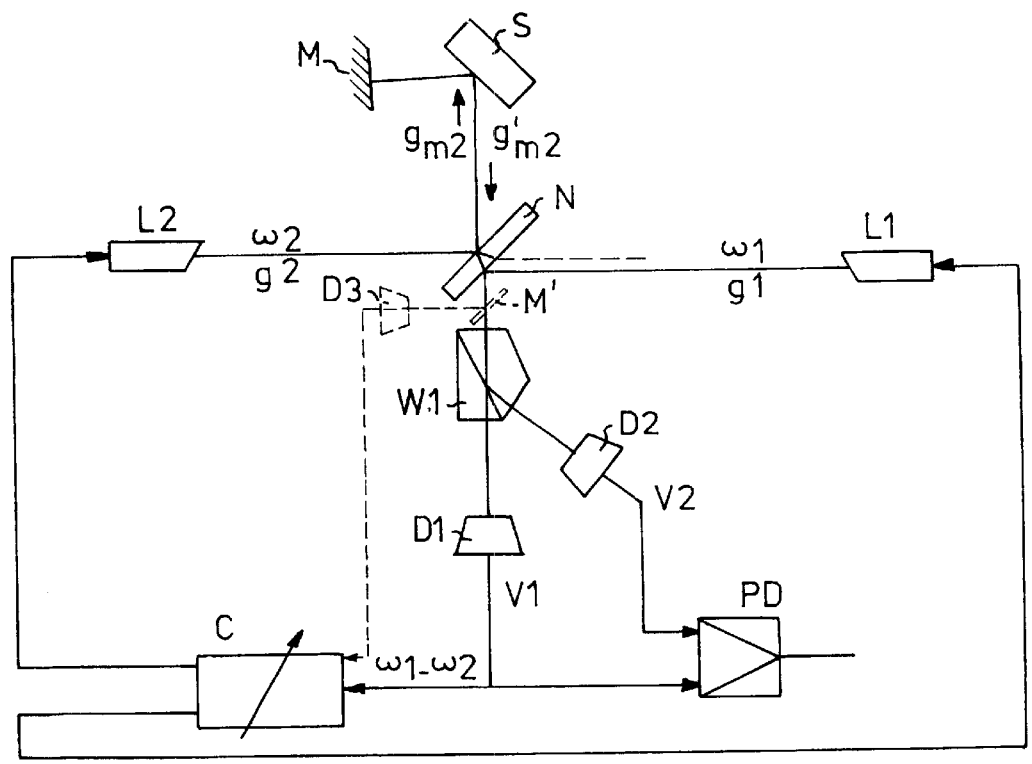
FIGS. 1a and 1b show ellipsometers according to the invention.

The ellipsometer shown in FIG. 1a comprises two light sources L1, L2 which preferably are laser sources. The light sources L1, L2 generate light beams $g_1$, $g_2$ with respective angular frequencies $\omega_1$, $\omega_2$.

The ellipsometer is also provided with a non-polarising beam splitter N which is provided with a front face and a rear face. The light beam $g_1$ is incident on the rear face of the beam splitter N. In the set-up according to FIG. 1a, the light beam $g_2$ is incident on the front face of the beam splitter N.

The light beam $g_2$ incident on the front face of the beam splitter N is as a result at least partially reflected in the direction of a sample S. Said reflected beam is indicated by $g_{m2}$.

The beam $g_{m2}$ is reflected by the surface of the sample S to be analysed. The beam reflected by the sample S is accurately autocollimated by a mirror M, which reflects the beam $g_{m2}$ towards the sample S. The beam $g_{m2}$ is thus reflected twice by the surface of the sample S, after which a measurement beam $g'_{m2}$ is produced which is shifted in phase and amplitude compared with the original beam $g_2$, the amplitude and phase shifts being dependent on the characteristics of the surface of the sample S.

The beam splitter N further deflects a portion of the light beam $g_2$ by means of refraction, as is indicated by a dotted line, at the rear face thereof. In this case nothing more is done with said deflected portion of the light beam $g_2$. However, it is pointed out that the light beams $g_1$ and $g_2$ must be aligned somewhat "off-line" so that the path, indicated by the dotted line, of that portion of the light beam $g_2$ transmitted by the beam splitter N is not coincident with the propagation path of the light beam $g_1$. Were this to be the case, the transmitted portion of the light beam $g_2$ would shine into the light source L1, which can give rise to instabilities.

The measurement beam $g'_{m2}$ is again incident on the front face of the beam splitter N in the manner indicated in FIG. 1a. At least a portion thereof will be transmitted by the beam splitter N and arrive at the rear face thereof via a refracted route.

The light beam $g_1$ is also incident at said point on the rear face of the beam splitter N, which light beam $g_1$ must have a phase with respect to the light beam $g_2$ such that interference with the measurement beam $g'_{m2}$ will occur at the rear face of the beam splitter N. As a result of the interference, an interference beam is produced which propagates in the direction of, for example, a Wollaston prism W1. The Wollaston prism W1 splits the orthogonal polarisation modes of the interference beam in accordance with the p and s directions, as is known to a person skilled in the art, and which directions, as is customary, are defined with respect to the sample S. The two orthogonal polarisation modes are picked up by a photodiode D1 and D2 respectively. The photodiodes D1, D2 convert the intensities of the two orthogonal polarisation modes into corresponding electrical alternating voltage signals V1, V2. The sine-wave shaped alternating voltage signals V1, V2 both have a frequency which is equal to the difference frequency between the frequencies of the light beams $g_1$ and $g_2$. Said difference frequency is also the measuring frequency of the ellipsometer. The amplitude ratio of the electrical alternating voltage signals V1, V2 and the phase difference between said two electrical alternating voltage signals supply the desired ellipsometric information about the sample S in terms of known angles $\Psi$ and $\Delta$.

The two light sources L1 and L2 can be ordinary commercially available stabilised He-Ne lasers. The frequency to which the light sources L1, L2 are tuned can be of the order of magnitude of 10 MHz.

In the embodiment according to FIG. 1a, the light sources L1, L2 are both controlled by a control circuit C, which can be adjusted by the user such that the difference between the frequencies of the light beams $g_1$ and $g_2$ can be set to a desired value. However, the control circuit does not have to be connected to both light sources L1, L2. In principle it suffices to control one of the two.

The electrical alternating voltage signals V1, V2 are fed to a phase detector PD. The phase detector PD can, for example, consist of a bridge circuit containing four diodes, which is known per se and can be constructed very inexpensively. Such a bridge circuit is not sensitive to the precise frequency of the alternating voltage signals V1, V2. The output signal from the phase detector is a measure for the parameter to be measured at the surface of the sample S. Further processing of the output signal from the phase detector PD can take place in any known manner and requires no further explanation here.

In the set-up according to FIG. 1a the electrical alternating voltage signal V1 is fed to one input of the control circuit C. Because the alternating voltage signal V1 has been derived from the abovementioned interference signal, it contains a component in which the difference between the angular frequencies $\omega_1$ and $\omega_2$ is present. This is fed as measurement signal to the control circuit. The control circuit C uses said input signal to stabilise the difference between the angular frequencies $\omega_1$ and $\omega_2$ to a specific value determined by the user. In principle, any desired circuit which is able to provide the desired functionality can be used for the control circuit C.

In the embodiment according to FIG. 1a, the input signal for the control circuit C is derived from the alternating voltage signal V1. The alternating voltage signal V2 likewise has a component which contains the difference between the angular frequencies $\omega_1$ and $\omega_2$. Therefore, the alternating voltage signal V2 can, as an alternative, also be fed to the control circuit C.

As a further alternative it is possible to supply a portion of the said interference signal as an optical signal to the control circuit. To this end, for example, a semi-transmitting mirror M' (shown in broken lines) can be arranged between the rear face of the beam splitter N and the Wollaston prism W1 to deflect a portion of the interference beam to a suitably chosen and set-up detector D3 (shown in broken lines), which is connected to the control circuit C. The output signal from such a detector then supplies the desired value $\omega_1 - \omega_2$. The alternating voltage signal V1 is then not fed to the control circuit.

Suitable control signals for the light sources L1 and/or L2 are then generated by the control circuit C on the basis of said input signal that contains $\omega_1 - \omega_2$. As has been stated, the value of said control signals can also be set by the user.

Figure 2:
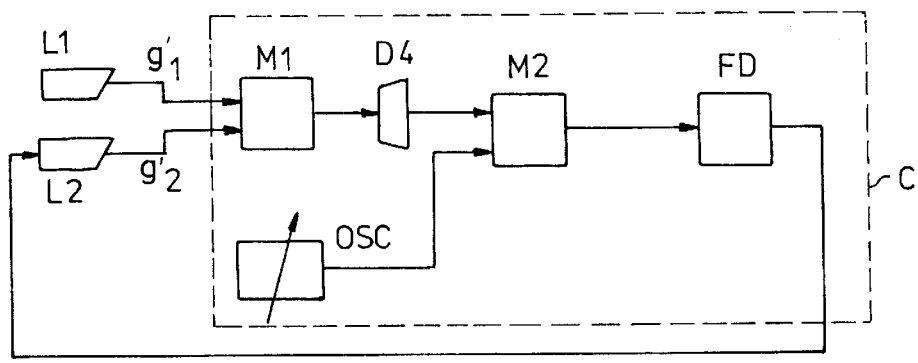
FIG. 2 shows a control circuit which can be used in the ellipsometer according to the invention.

FIG. 2 shows a possible control circuit C which could be used in the ellipsometer according to the invention. However, the control circuit C according to FIG. 2 does not fit directly in the set-up shown in FIG. 1a because said control circuit uses optical input signals $g'_1$ and $g'_2$ as input signal whereas in the set-up according to FIG. 1a the electrical input signal V1 is used. The optical input signals $g'_1$ and $g'_2$ are derived from the light beams $g_1$ and $g_2$ respectively. This can be effected, for example, by deflecting portions of the light beams $g_1$ and $g_2$ using semi-transmitting mirrors (not shown), the deflected portions being $g'_1$ and $g'_2$.

The set-up shown in FIG. 2 corresponds to a set-up which is described in U.S. Pat. No. 5,396,361 and has been discussed in the preamble to the description above. The known set-up contains two laser sources L1, L2, which generate laser beams $g'_1$, $g'_2$, respectively. The two laser beams $g'_1$, $g'_2$ are fed to a multiplier M1, which performs a heterodyne detection. The output signal from the multiplier M1 is fed to a detector D4, which provides an electrical output signal. The output from the detector D4 is coupled to one input of a further multiplier M2. Another input of the further multiplier M2 is coupled to an oscillator OSC, which provides a reference signal. The multiplier M2 multiplies the two input signals, so that a signal having a difference frequency component is produced which is a measure for the difference between the frequencies of the output signal from the detector D4 and the reference signal originating from the oscillator OSC. The output of the multiplier M2 is coupled to a frequency discrimination circuit FD. The output signal from the frequency discrimination circuit FD is fed to at least one of the two laser sources L1, L2 in order to keep the difference between the optical frequencies of the laser sources L1, L2 at least virtually constant. In the set-up according to FIG. 2, the components M1, D4, M2, OSC and FD together form the control circuit C.

In the set-up according to the invention, the frequency of the reference signal, which is produced by the oscillator OSC, can be controlled by the user. This provides a user of the ellipsometer according to the invention with a high measure of flexibility.

Figure 1B:
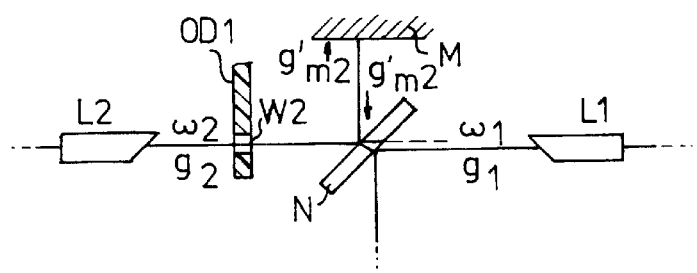

In one embodiment of the invention the ellipsometer is suitable for reading optical information from optical information carriers. FIG. 1b shows an alternative set-up to the set-up according to FIG. 1a for this purpose, although only the most essential elements are shown again in FIG. 1b. The other elements are the same as in FIG. 1a. In FIG. 1b an optical disc OD1 is located between the light source L2 and the neutral beam splitter N. The optical disc OD1 is provided with optical information, for example in the form of wells, one of which W2 is shown on an enlarged scale.

The light beam $g_2$ moves through the well W2 (that is to say the optical disc OD1 has transmission characteristics) to the neutral beam splitter N. The measurement beam $g'_{m2}$ is thus formed. At least-a portion of the measurement beam $g'_{m2}$ is reflected at the front face of the neutral beam splitter N in the direction of a mirror M, which reflects the measurement beam $g'_{m2}$ again towards the front face of the neutral beam splitter N.

In the same way as in the set-up according to FIG. 1a, an interference beam is thus formed at the rear face of the neutral beam splitter N by interference with the light beam $g_1$, which interference beam will propagate in the direction of, for example, the Wollaston prism W1.

The optical disc OD1 can be driven in a known manner by drive means, which are not shown. In practice, the light source L2 will then be a laser source which can be moved laterally over the surface of the optical disc OD1 so that the wells, which, for example, are arranged in a groove form, can be scanned.

FIGS. 3a to 3d show various ways in which an optical disc can be scanned.

Figure 3A:
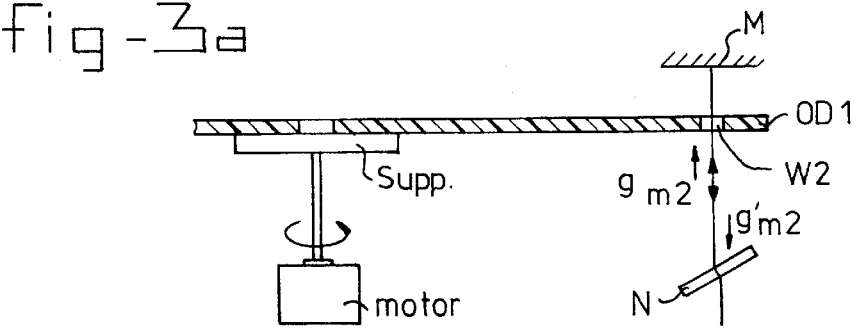
FIGS. 3a, 3b, 3c and 3d show optical information carriers which can be scanned with the aid of the ellipsometer according to the invention.

FIG. 3a shows the situation where an optical disc OD1 with transmission characteristics is used. It is also indicated that the optical disc OD1 is then arranged such that the light beam $g_{m2}$ originating from the front face of the neutral beam splitter N impinges on the well W2 in order then to return, following reflection through an angle of 180°, as measurement beam $g'_{m2}$.

Figure 3B:
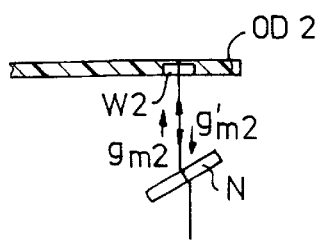

FIG. 3b shows an optical disc OD2 which has reflection characteristics instead of transmission characteristics. The well W2 now reflects the beam $g_{m2}$ and thus forms the measurement beam $g'_{m2}$ directly.

Figure 3C:
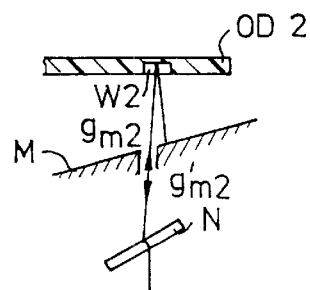

The reflecting optical disc OD2 has been drawn again in FIG. 3c, but now in a set-up in which the beam $g_{m2}$ impinges on the surface of the reflecting optical disc OD2 not orthogonally but at an angle which is somewhat smaller than 90°. Following reflection by the well W2, the beam is then incident on a mirror M, which reflects the beam through an angle of 180° to the well W2. The measurement beam $g'_{m2}$ is then produced, which measurement beam is directed onto the front face of the neutral beam splitter N, just as in the set-up according to FIG. 1a. There is a hole in the mirror M to provide the propagation path for the beams between the neutral beam splitter N and the optical disc OD2. The advantage of the set-up shown in FIG. 3c is that the beam scans the well W2 twice.

Figure 3D:
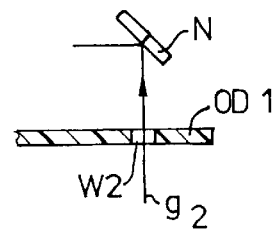

For the sake of completeness, FIG. 3d shows the situation as already shown in FIG. 1b once again.

Furthermore, for the sake of completeness it is indicated in FIG. 3d that the optical disc OD1 will in practice be supported by suitable support means Supp., which during operation are driven by a motor.

Figure 4A:
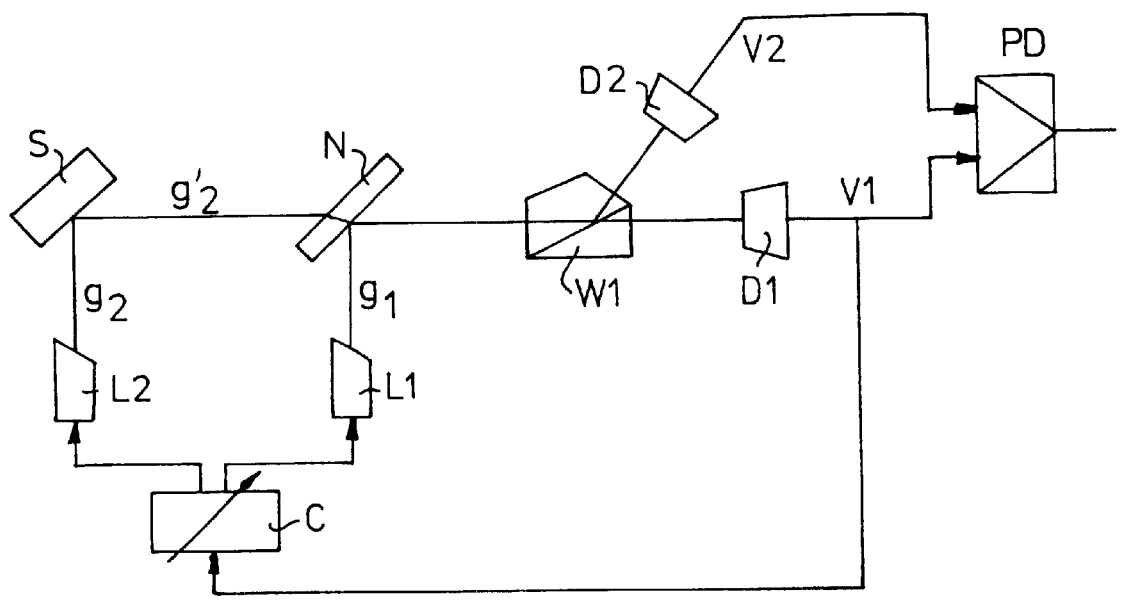
FIGS. 4a and 4b show alternative ellipsometers according to the invention.

FIG. 4a shows an alternative set-up to the set-up according to FIG. 1a. The difference compared with the set-up according to FIG. 1a is that the light beam $g_2$ originating from the light source L2 is first incident on the sample S in order to form a measurement beam $g'_2$ which is incident on the front of the neutral beam splitter N. After transmission through the neutral beam splitter N, the measurement beam $g'_2$ interferes with the light beam $g_1$, which is directed by the light source L1 onto the rear face of the neutral beam splitter N. The interference beam thus produced propagates in the direction of the Wollaston prism W1.

The remainder of the set-up according to FIG. 4a is the same as the set-up in FIG. 1a and is not repeated here. It is obvious that in the set-up according to FIG. 4a as well it is not necessary for the alternating voltage signal V1 to be fed to the control circuit C. Instead of this, use can be made of the partially transmitting mirror M' and the detector D3, which have already been shown in FIG. 1a by way of an alternative.

Furthermore, it will be clear to those skilled in the art that the set-up according to FIG. 4a can be adjusted such that the control circuit according to FIG. 2, or variants thereof, can be used. This can be effected in the manner described previously with reference to FIG. 2.

Figure 4B:
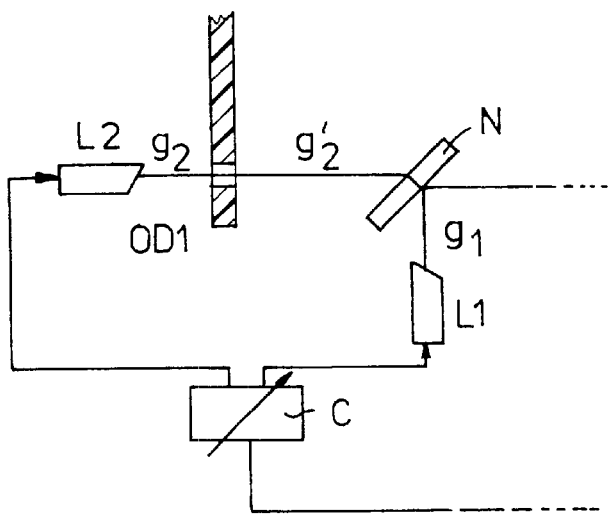

The set-up according to FIG. 4a can also be used for reading optical information on an optical disc OD1 having transmission characteristics. A set-up suitable for this purpose is shown in FIG. 4b. The set-up shown in FIG. 4b shows only a few essential components. The remaining components are the same as in the set-up according to FIG. 4a or as in the variants thereof indicated above.

It is obvious that the invention is not restricted to the embodiments which are shown in the figures. The set-up of the various components can be changed, in which context the radiation path of the various beams can be changed with the aid of mirrors and/or other optical components if this is advantageous for specific applications. Furthermore, the neutral beam splitter can be a neutral Curie or a non-polarising beam splitter. The scope of the present invention is limited only by the appended claims.

What is claimed is:

1. Ellipsometer at least comprising
light source means (L1, L2) which during operation provide a first light beam ($g_1$) having a first angular frequency ($\omega_1$) and a second light beam ($g_2$) having a second angular frequency ($\omega_2$),
a neutral beam splitter N having a front face for receiving and at least partially transmitting a measurement beam ($g'_{m2}$), which, during operation, is produced by scanning a sample (S; OD1; OD2) with the second light beam ($g_2$), and a rear face for receiving the first light beam ($g_1$), wherein, during operation, the measurement beam ($g'_{m2}$) interferes with the first light beam ($g_1$) at the rear face and an interference beam is thus formed,
a unit (W1) for receiving the interference beam, separating the orthogonal components of the interference beam and providing two alternating voltages (V1, V2) corresponding thereto,
characterized in that the light source means comprise a first laser source (L1) for only producing first light beam ($g_1$) and a separate laser source (L2) for only producing second light beam ($g_2$) and in that the ellipsometer is also provided with a control circuit (C) having at least one input for receiving information with regard to either the first and second angular frequencies ($\omega_2$, $\omega_1$) or the difference between the first and second angular frequencies and at least one output, coupled at least to one of the two laser sources, for controlling the difference between the first and second angular frequencies ($\omega_2$, $\omega_1$).

2. Ellipsometer according to claim 1, characterized in that the front face of the neutral beam splitter (N) is set up to receive the second light beam ($g_2$), at least partially reflect the second light beam ($g_2$) in the direction of the sample (S; CD1; CD2) to be scanned and then receive and at least partially transmit the measurement beam ($g'_{m2}$) originating from the sample (S; CD1; CD2) to be scanned.

3. Ellipsometer according to claim 1, characterized in that the control circuit (C) receives ne of the two alternating voltages (V1, V2) at its input.

4. Ellipsometer according to claim 1, characterized in that said ellipsometer is provided with a partially transmitting mirror (M') for partially deflecting the interference beam, and a detector (D3) that is coupled to the control circuit (C) and is set up to receive the partially deflected interference beam.

5. Ellipsometer according to claim 1, characterized in that the control circuit (C) receives at its input a first input signal ($g'_1$) derived from the first light beam ($g_1$) and a second input signal ($g'_2$) derived from the second light beam ($g_2$).

6. Ellipsometer according to claim 1, characterized in that the at least one output of the control circuit is coupled to both the first and the second laser.

7. Ellipsometer according to claim 1, characterized in that the said ellipsometer is also provided with a support (Supp.) for supporting an optical information carrier (OD1; OD2).

* * * * *